(12) United States Patent
Bly (10) Patent No.: US 7,917,230 B2
(45) Date of Patent: Mar. 29, 2011

(54) NEUROSTIMULATING LEAD HAVING A STENT-LIKE ANCHOR

(75) Inventor: Mark J. Bly, Falcon Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 368 days.

(21) Appl. No.: 11/668,834

(22) Filed: Jan. 30, 2007

(65) Prior Publication Data

US 2008/0183253 A1 Jul. 31, 2008

(51) Int. Cl.
*A61N 1/05* (2006.01)
(52) U.S. Cl. ........................................ 607/116; 607/125
(58) Field of Classification Search .................. 607/116, 607/122, 123, 125
See application file for complete search history.

(56) References Cited

U.S. PATENT DOCUMENTS

| | | |
|---|---|---|
| 4,365,634 A | 12/1982 | Bare et al. |
| 4,414,986 A | 11/1983 | Dickhudt et al. |
| 4,774,949 A | 10/1988 | Fogarty |
| 4,905,667 A | 3/1990 | Foerster et al. |
| 4,920,979 A | 5/1990 | Bullara |
| 4,944,088 A | 7/1990 | Doan et al. |
| 5,016,808 A | 5/1991 | Heil, Jr. et al. |
| 5,221,261 A | 6/1993 | Termin et al. |
| 5,265,608 A | 11/1993 | Lee et al. |
| 5,330,515 A | 7/1994 | Rutecki et al. |
| 5,351,394 A | 10/1994 | Weinberg |
| 5,378,239 A | 1/1995 | Termin et al. |
| 5,383,922 A | 1/1995 | Zipes et al. |
| 5,387,233 A | 2/1995 | Alferness et al. |
| 5,411,546 A | 5/1995 | Bowald et al. |
| 5,423,865 A | 6/1995 | Bowald et al. |
| 5,476,498 A | 12/1995 | Ayers |
| 5,496,277 A | 3/1996 | Termin et al. |
| 5,531,779 A * | 7/1996 | Dahl et al. ................. 607/119 |
| 5,540,730 A | 7/1996 | Terry, Jr. et al. |
| 5,755,714 A | 5/1998 | Murphy-Chutorian |
| 5,755,761 A | 5/1998 | Obino |
| 5,766,203 A | 6/1998 | Imran et al. |
| 5,792,187 A | 8/1998 | Adams |
| 5,803,928 A | 9/1998 | Tockman et al. |

(Continued)

FOREIGN PATENT DOCUMENTS

DE 10103288 8/2002

(Continued)

OTHER PUBLICATIONS

Tarver et al., "Clinical Experience with a Helical Bipolar Stimulating Lead," PACE, October, Part II 1992, pp. 1545-1556, vol. 15, Cyberonics, Inc., Webster, Texas and the Department of Neurosurgery, Baylor College of Medicine.

(Continued)

*Primary Examiner* — Michael Kahelin
(74) *Attorney, Agent, or Firm* — Faegre & Benson LLP (57) ABSTRACT

A neuron stimulating lead having a stent-like anchor is described. A distal portion of the lead is mounted to an exterior of the lead anchor. The stent-like lead anchor is formed from a superelastic material and is adapted to transition from a collapsed configuration to an expanded configuration upon deployment in a vessel. In the expanded configuration, the lead anchor presses the distal portion of the lead against at least one vessel wall of a vessel in which the lead is deployed securing and stabilizing the distal portion of the lead within the vessel.

25 Claims, 8 Drawing Sheets

U.S. PATENT DOCUMENTS

| | | |
|---|---|---|
| 5,871,531 A | 2/1999 | Struble |
| 5,954,761 A | 9/1999 | Machek et al. |
| 5,997,536 A * | 12/1999 | Osswald et al. ............... 606/47 |
| 6,006,134 A | 12/1999 | Hill et al. |
| 6,021,354 A | 2/2000 | Warman et al. |
| 6,055,456 A | 4/2000 | Gerber |
| 6,292,695 B1 | 9/2001 | Webster, Jr. et al. |
| 6,321,123 B1 | 11/2001 | Morris et al. |
| 6,363,288 B1 | 3/2002 | Bush et al. |
| 6,385,492 B1 | 5/2002 | Ollivier et al. |
| 6,397,109 B1 | 5/2002 | Cammilli et al. |
| 6,429,217 B1 | 8/2002 | Puskas |
| 6,442,413 B1 * | 8/2002 | Silver ............................ 600/345 |
| 6,449,507 B1 | 9/2002 | Hill et al. |
| 6,516,232 B2 | 2/2003 | Skinner |
| 6,564,096 B2 | 5/2003 | Mest |
| 6,584,362 B1 | 6/2003 | Scheiner et al. |
| 6,600,956 B2 | 7/2003 | Maschino et al. |
| 6,656,960 B2 | 12/2003 | Puskas |
| 6,671,562 B2 | 12/2003 | Osypka et al. |
| 6,766,203 B2 | 7/2004 | Doan et al. |
| 6,778,854 B2 | 8/2004 | Puskas |
| RE38,654 E | 11/2004 | Hill et al. |
| RE38,705 E | 2/2005 | Hill et al. |
| 6,882,887 B1 | 4/2005 | Shelchuk et al. |
| 6,889,092 B2 | 5/2005 | Zhu et al. |
| 6,901,297 B2 | 5/2005 | Frericks et al. |
| 6,934,583 B2 | 8/2005 | Weinberg et al. |
| 6,934,589 B2 | 8/2005 | Sundquist et al. |
| 6,973,340 B2 * | 12/2005 | Fuimaono et al. ............ 600/374 |
| 7,047,084 B2 | 5/2006 | Erickson et al. |
| 7,058,454 B1 | 6/2006 | Chitre et al. |
| 7,676,275 B1 | 3/2010 | Farazi et al. |
| 2002/0026228 A1 | 2/2002 | Schauerte |
| 2002/0032963 A1 | 3/2002 | Lindegren |
| 2002/0087192 A1 | 7/2002 | Barrett et al. |
| 2002/0151949 A1 | 10/2002 | Dahl et al. |
| 2002/0183237 A1 | 12/2002 | Puskas |
| 2002/0183817 A1 | 12/2002 | Van Venrooij et al. |
| 2002/0198570 A1 | 12/2002 | Puskas |
| 2002/0198571 A1 | 12/2002 | Puskas |
| 2003/0074039 A1 | 4/2003 | Puskas |
| 2003/0078623 A1 | 4/2003 | Weinberg et al. |
| 2003/0195506 A1 | 10/2003 | Stewart et al. |
| 2003/0195603 A1 | 10/2003 | Scheiner et al. |
| 2003/0199961 A1 * | 10/2003 | Bjorklund et al. ............ 607/126 |
| 2003/0229380 A1 | 12/2003 | Adams et al. |
| 2004/0015204 A1 | 1/2004 | Whitehurst et al. |
| 2004/0015205 A1 | 1/2004 | Whitehurst et al. |
| 2004/0019359 A1 | 1/2004 | Worley et al. |
| 2004/0019377 A1 | 1/2004 | Taylor et al. |
| 2004/0030362 A1 | 2/2004 | Hill et al. |
| 2004/0059383 A1 | 3/2004 | Puskas |
| 2004/0059404 A1 | 3/2004 | Bjorklund et al. |
| 2004/0062852 A1 | 4/2004 | Schroeder et al. |
| 2004/0133240 A1 | 7/2004 | Adams et al. |
| 2004/0147825 A1 | 7/2004 | Milojevic et al. |
| 2004/0172075 A1 | 9/2004 | Shafer et al. |
| 2004/0172088 A1 | 9/2004 | Knudson et al. |
| 2004/0176782 A1 | 9/2004 | Hanse et al. |
| 2004/0186531 A1 | 9/2004 | Jahns et al. |
| 2004/0260374 A1 | 12/2004 | Zhang et al. |
| 2005/0038489 A1 | 2/2005 | Grill |
| 2005/0060015 A1 | 3/2005 | Tanaka |
| 2005/0065553 A1 | 3/2005 | Ben Ezra et al. |
| 2005/0080472 A1 * | 4/2005 | Atkinson et al. .............. 607/126 |
| 2005/0113862 A1 | 5/2005 | Besselink et al. |
| 2005/0131467 A1 | 6/2005 | Boveja |
| 2005/0143412 A1 | 6/2005 | Puskas |
| 2005/0149126 A1 | 7/2005 | Libbus |
| 2005/0149155 A1 | 7/2005 | Scheiner et al. |
| 2005/0197675 A1 | 9/2005 | David et al. |
| 2005/0251239 A1 * | 11/2005 | Wallace et al. ............... 607/126 |
| 2006/0206153 A1 | 9/2006 | Libbus et al. |
| 2006/0229677 A1 | 10/2006 | Moffitt et al. |
| 2006/0241737 A1 | 10/2006 | Tockman et al. |
| 2006/0259085 A1 | 11/2006 | Zhang et al. |
| 2006/0259107 A1 | 11/2006 | Caparso et al. |
| 2008/0051861 A1 | 2/2008 | Cross et al. |
| 2008/0183186 A1 | 7/2008 | Bly et al. |
| 2008/0183187 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |

FOREIGN PATENT DOCUMENTS

| | | |
|---|---|---|
| EP | 0453117 | 10/1991 |
| EP | 0795343 | 9/1997 |
| EP | 1304135 | 4/2003 |
| JP | 05049701 A | 3/1993 |
| WO | 8304181 | 12/1983 |
| WO | 9956817 | 11/1999 |
| WO | 0100273 A1 | 1/2001 |
| WO | 0218006 | 3/2002 |
| WO | 2006098996 | 9/2006 |

OTHER PUBLICATIONS

Li et al., "Vagal Nerve Stimulation Markedly Improves Long-Term Survival After Chronic Heart Failure in Rats," Circulation Journal of the American Heart Asscociation, Dec. 8, 2003, pp. 120-124.

International Search Report and Written Opinion of international application No. PCT/US2008/051700, mailed Jun. 25, 2008, 13 pp.

Nabutovsky et al., "Lead Design and Initial Applications of a New Lead for Long-Term Endovascular Vagal Stimulation," PACE, vol. 30, Jan. 2007 Supplement 1, pp. S215-S218.

Website, Guidant Fineline II Sterox and Fineline IISterox EZ, http://www/guidant.com/products/producttemplates/crm/fineline_II_sterox.shtml, 2004, Guidant Corporation, Aug. 26, 2004, 3 pages.

* cited by examiner

NEUROSTIMULATING LEAD HAVING A STENT-LIKE ANCHOR

CROSS-REFERENCE TO RELATED APPLICATIONS

This application is related to the following co-pending and co-owned applications: SPIRAL CONFIGURATIONS FOR INTRAVASCULAR LEAD STABILITY, filed on Jan. 30, 2007 and assigned Ser. No. 11/668,926; DUAL SPIRAL LEAD CONFIGURATIONS, filed on Jan. 30, 2007 and assigned Ser. No. 11/668,887; ELECTRODE CONFIGURATIONS FOR TRANSVASCULAR NERVE STIMULATION, filed on Jan. 30, 2007 and assigned Ser. No. 11/668,957; TRANSVASCULAR LEAD WITH PROXIMAL FORCE RELIEF, filed on Jan. 30, 2007 and assigned Ser. No. 11/669,039; METHOD AND APPARATUS FOR DELIVERING A TRANSVASCULAR LEAD, filed on Jan. 30, 2007 and assigned Ser. No. 11/669,042; METHOD AND APPARATUS FOR DIRECT DELIVERY SYSTEM FOR OF TRANSVASCULAR LEAD, filed on Jan. 30, 2007 and assigned Ser. No. 11/669,047; SIDE PORT LEAD DELIVERY SYSTEM, filed on Jan. 30, 2007 and assigned Ser. No. 11/669,050, all of which are herein incorporated by reference.

TECHNICAL FIELD

The present invention relates to medical electrical leads for nerve or muscle stimulation. More specifically, the present invention relates to medical electrical lead anchors for stabilizing leads in an intravascular location adjacent a nerve to be stimulated.

BACKGROUND

A significant amount of research has been directed both to the direct and indirect stimulation of nerves including the left and right vagus nerves, the sympathetic and parasympathetic nerves, the phrenic nerve, the sacral nerve, and the cavernous nerve to treat a wide variety of medical, psychiatric, and neurological disorders or conditions. More recently, stimulation of the vagus nerve has been proposed as a method for treating various heart conditions, including heart failure.

Typically in the past, nerve stimulating electrodes were cuffs placed in direct contact with the nerve to be stimulated. A much less invasive approach is to stimulate the nerve through an adjacent vein using an intravascular lead. A lead including one or more electrodes is inserted into a patient's vasculature and delivered at a site within a vessel adjacent a nerve to be stimulated. However, without any additional means of stabilizing the lead within the vein, the lead can move and/or rotate causing the electrodes to migrate from the stimulation site.

Thus, there is a need in the art for a mechanism to minimize intravascular lead rotation and movement and allow for consistent and reliable delivery of chronic therapy.

SUMMARY

According to one embodiment of the present invention, a medical electrical lead for stimulating a nerve includes: a conductive lead body having a proximal end adapted to be connected to a pulse generator; a distal portion including at least one electrode adapted to deliver an electrical pulse across a vessel wall; and a lead anchor. The lead anchor is adapted to expand from a collapsed configuration to a preformed, expanded configuration, wherein in the collapsed configuration the distal portion has an effective length substantially equal to the effective length of the collapsed lead anchor. The distal portion is coupled to an exterior of the lead anchor such that in the expanded configuration the lead anchor presses the distal portion of the lead against at least one vessel wall of a vessel in which the lead is deployed securing and stabilizing the distal portion of the lead within the vessel.

According to another embodiment of the present invention, a medical electrical lead for stimulating a nerve from within an adjacent vessel includes: a proximal end adapted to be connected to a pulse generator; a distal portion including at least one electrode adapted to deliver an electrical pulse across a vessel wall; and a lead anchor adapted to expand from a collapsed configuration to a preformed, expanded configuration. The distal portion is coupled to an exterior of the lead anchor.

According to another embodiment of the present invention, a lead anchor assembly for securing and stabilizing a lead within a vessel includes a lead anchor including at least a first end secured to a lead body and a plurality of integrally formed struts extending from the first end secured to the lead body to a second end. The lead anchor can be formed from a laser cut tube of a superelastic material.

A method of stimulating a nerve from within an adjacent vessel is also described. According to one embodiment of the present invention, the method includes providing a medical electrical lead including a lead anchor assembly. A distal portion of the lead mounted to an exterior of the anchor. The lead anchor includes at least a first end secured to a lead and a plurality of struts extending from the first end to a second end and is adapted to expand from a collapsed configuration to a preformed, expanded configuration such that the distal portion of the lead is pressed up against a wall of the vessel. Additionally, the method includes advancing the lead through a patient's vasculature system to a stimulation site located within the vessel; partially deploying the lead anchor assembly such that at least one electrode is exposed; temporarily stimulating the nerve using the partially deployed lead assembly; and determining an optimal stimulation threshold. The method further includes fully deploying the lead anchor assembly and chronically stimulating the adjacent nerve from a stimulation site located with the vessel.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

While the embodiments described herein generally refer to placement of a lead into the right internal jugular vein through the right or left subclavian vein, the various embodiments of the present invention as described below can be practiced at numerous sites within a patient's vasculature system. Any intravascular site that is adjacent to a nerve, muscle, or brain tissue that has the potential to benefit from stimulation is a potential site for stimulation. The term "vessel" includes all veins and arteries of the circulatory system. Additionally, the term "vessel" includes various structures of the lymphatic system, including lymph nodes, ducts, capillaries, and vessels. Likewise, as used herein, the term "vessel" also includes the various tube-like structures of the gastrointestinal system. The terms "nerve" and "nerve fiber" as used herein include a single neuron, nerve, nerve ending(s), or nerve bundle. The term "intravascular" means within a vessel including the veins and arteries of the circulatory system. When referring to "intravascular stimulation" in describing the embodiments of the present invention, it is meant to refer to stimulation from within the circulatory system resulting in (transvascular) stimulation of a nerve, muscle, or tissue of interest. The term "transvascular" means across a vessel or vessel wall. "Stimulation" means a stimulus, usually electrical, which causes depolarization of a cell or cells, or portion of a cell, contraction, excitation as measured by, e.g., calcium or sodium influx into the cell, or an altered membrane potential across a cell.

Vessels having sufficient diameter for catheter access which are known to have nerves running adjacent to or nearby are suitable candidates for potential stimulation sites. Exemplary sites include, but are not limited to, the following: the left and right internal jugular veins, the azygous vein, the brachiocephalic (innominate) vein, the subclavian vein, the superior vena cava, the pulmonary artery, and cardiac branch vessels. Other potential stimulation sites include, but are not limited to, the following: thoracic duct, the bile duct, and sites along the upper gastrointestinal and lower gastrointestinal tracts. Exemplary nerves to be stimulated include, but are not limited to, the following: the left and right vagus nerves, the phrenic nerve, the parasympathetic nerves, the sympathetic nerves, and the sacral nerve.

Figure 1:
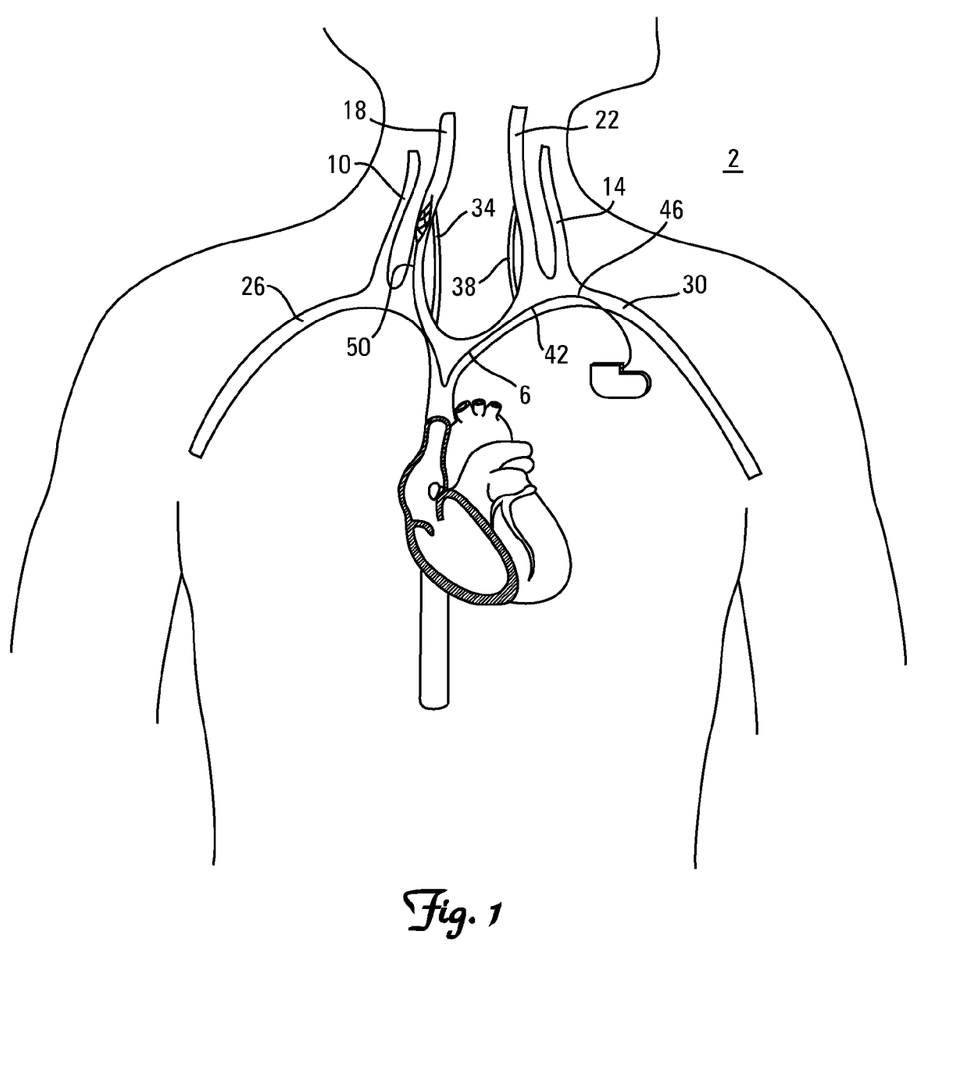
FIGS. 1 and 2 are schematic views of a lead deployed in a patient's internal jugular vein at a location adjacent the vagus nerve according to an embodiment of the present invention.
Figure 2:
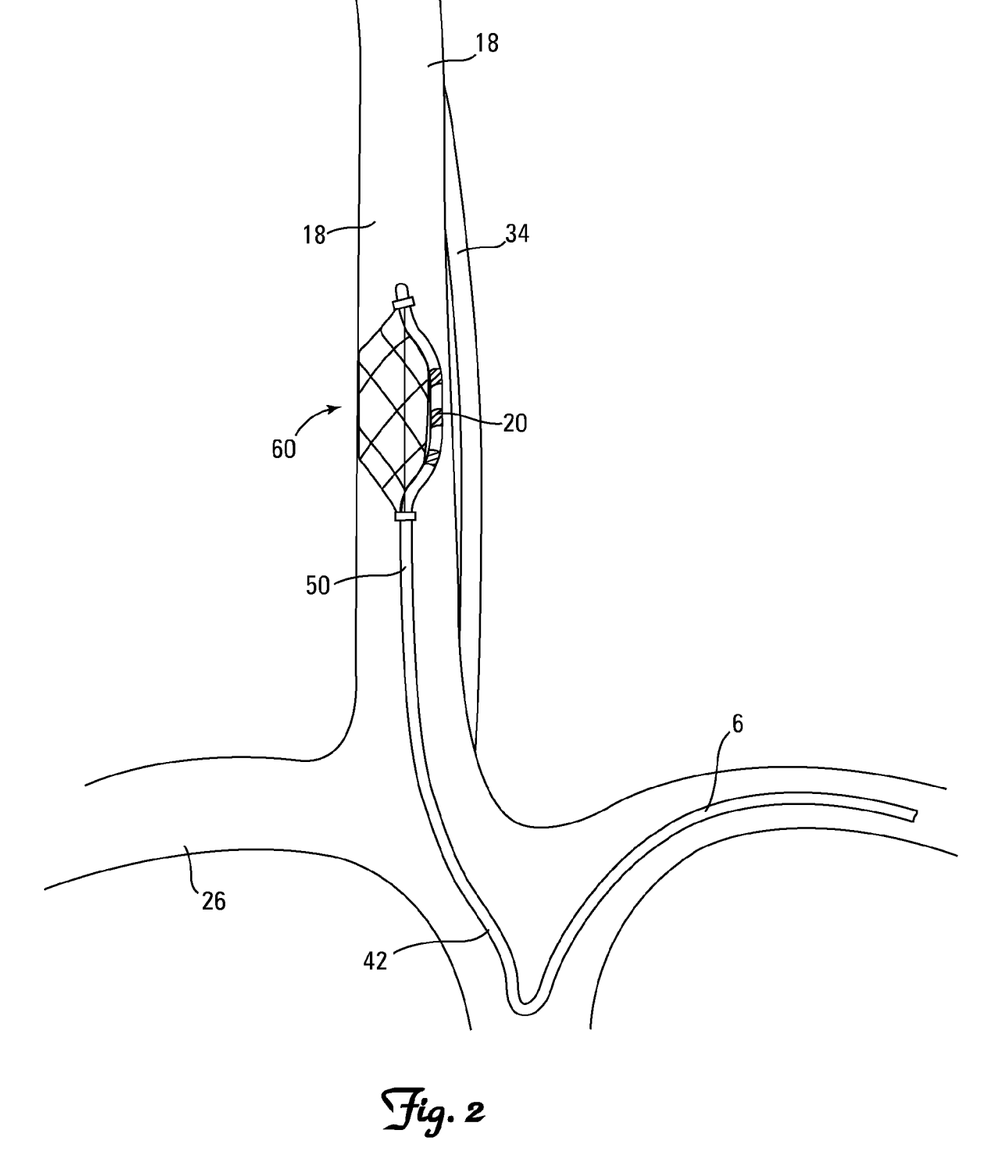

FIG. 1 shows a perspective view of a patient's vascular system 2 including a lead 6 deployed within the system 2. FIG. 2 is a close-up schematic view of the lead 6 deployed within the system 2. In general, the vascular system 2, as shown, includes the right and left external jugular veins 10 and 14, the right and left internal jugular veins 18 and 22, the right and left subclavian veins 26 and 30, portions of which are generally aligned with the right and left vagus nerves 34 and 38. As shown in FIGS. 1 and 2, the lead 6 is inserted into a patient's vasculature system through the left subclavian vein 30 and into the right internal jugular vein 18. The lead 6 is positioned in the right internal jugular vein 18 adjacent to the right vagus nerve 34. Alternatively, the lead 6 can be inserted and advanced to a stimulation site within the right internal jugular vein 18 via the right subclavian vein 26.

The lead 6 includes a lead body 42 including a proximal end and a distal portion 50. One or more electrodes 56 are positioned along the lead body 42. In particular, the electrodes 56 are located on the distal portion 50 of the lead 6. The proximal end of the lead is adapted to be connected to a pulse generator or other implantable device. The lead body 42 is flexible, and typically has a circular cross-section.

According to another embodiment of the present invention, the lead body 42 includes a plurality of conductors including individual wires, coils, or cables. The conductors can be insulated and/or molded in place with an insulator such as silicone, polyurethane, ethylene tetrafluoroethylene, or another biocompatible, insulative polymer. In one exemplary embodiment, the lead body 42 has a co-radial design. In this embodiment, each individual conductor is separately insulated and then wound together in parallel to form a single coil. In another exemplary embodiment, the lead body 42 is co-axial. According to a further embodiment of the present invention, each conductor is adapted to connect to an individual electrode 56 in a one-to-one manner allowing each electrode 56 to be individually addressable. In yet a further embodiment of the present invention, the lead body 42 includes a lumen adapted to receive a guiding element such as a guide wire or a stylet.

The lead 6 also includes a distal portion 50. The distal portion 50 can have a similar or different construction than the lead body 42. According to one embodiment, the distal portion 50 of the lead 6 is stiffer than the lead body 42. One exemplary embodiment of such a structure is disclosed in commonly assigned and co-pending application entitled "TRANSVASCULAR LEAD WITH PROXIMAL FORCE RELIEF", assigned Ser. No. 11/669,039, which is herein incorporated by reference. According to another embodiment of the present invention, the distal portion 50 includes a material, which may impart a desired shape useful for anchoring or securing the distal portion 50 of the lead 6 in a vessel. Exemplary materials include Nitinol and other materials known in the art.

The distal portion 50 includes a lead anchor 60. As shown in FIGS. 3A-4C, the distal portion 50 of the lead 6 is mounted to an exterior 64 of the lead anchor 60. The distal portion 50 is mounted to the anchor 60 using a variety of means including adhesives, welding, suturing or otherwise bonding the distal portion 50 to the lead anchor 60.

Figure 3A:
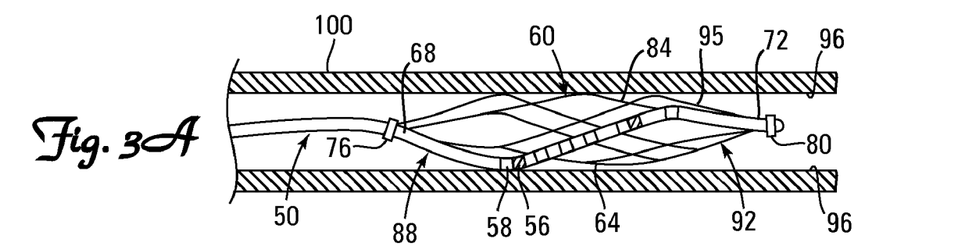
FIGS. 3A-3D are schematic views of a distal portion of a lead including a lead anchor including tapered proximal and distal ends deployed within a vessel according to various embodiments of the present invention.
Figure 3B:
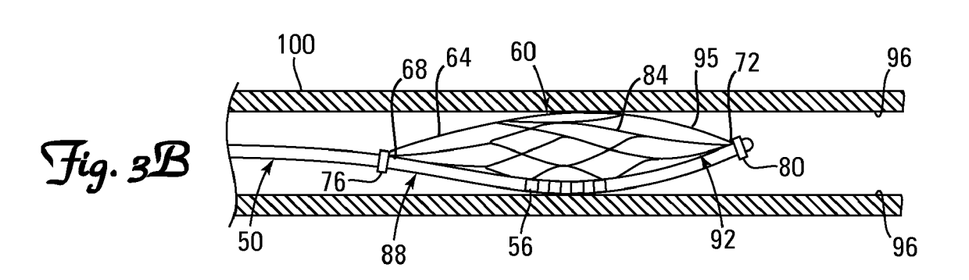
Figure 3C:
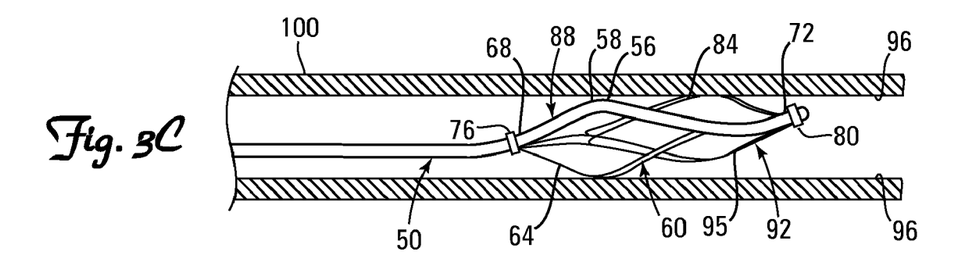
Figure 3D:
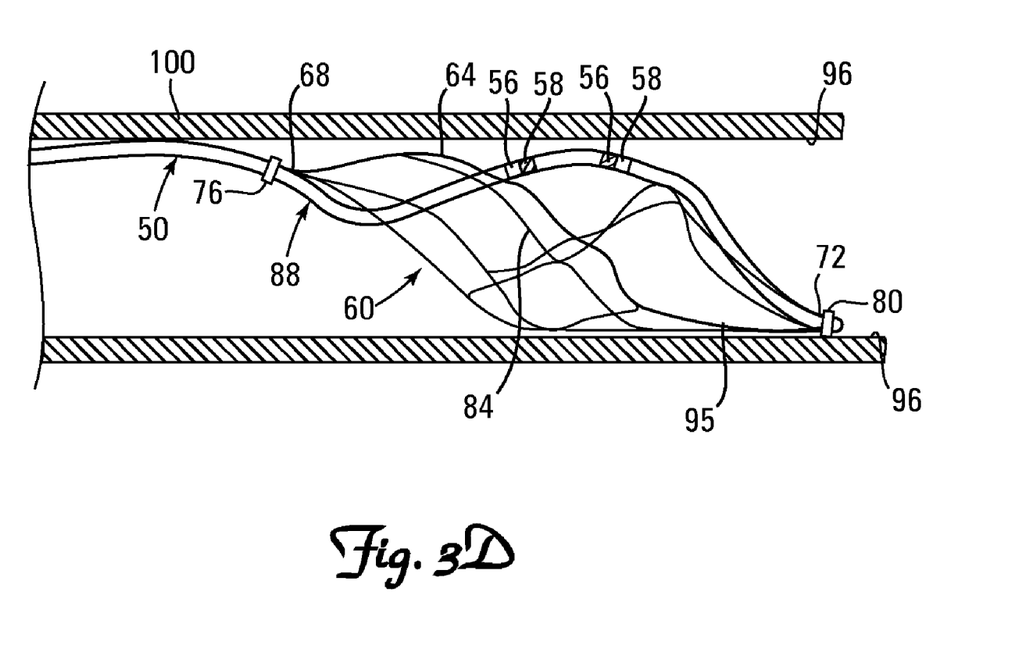

The distal portion 50 can be mounted to the lead anchor 60 such that it follows a curvature of a strut forming the anchor 60, as shown in FIGS. 3A, 3C, 4A, and 4B. Alternatively, the distal portion 50 can be mounted such that it is substantially straight along the length of the anchor 60, as shown in FIGS. 3B and 4C. According to another embodiment of the present invention, the distal portion 50 of the lead 6 is mounted to the exterior 64 of the lead anchor 60 such that a first end 68 of the distal portion 50 of the lead 6 is generally aligned with a second end 72 (shown in FIGS. 3A-3C). More particularly, in these embodiments, the distal portion 50 of the lead is mounted to the exterior 64 such that the first end 68 is radially aligned with the second end 72. Alternatively, the distal portion 50 of the lead 6 is mounted to the exterior 64 of the lead anchor such that the first end 68 of the distal portion 50 of the lead 6 is radially offset from the second 62, for example as shown in FIG. 3D.

According to another exemplary embodiment, the distal portion 50 is bifurcated. The bifurcated distal portion 50 includes a first elongate member and a second elongate member. Each elongate member of the bifurcated distal portion is mounted to an exterior of the lead anchor 60. The elongated members can each follow a curvature of a strut forming the anchor 60. Alternatively, the elongated members can be mounted such that they are substantially straight along the length of the anchor. According to yet another example, an elongated member can follow a curvature of a strut with the other elongate member mounted such that it is substantially straight along the length of the anchor 60.

According to another exemplary embodiment of the present invention, the distal portion 50 can include one or more recesses in an outer layer of the lead body 42. The recesses are adapted to receive a portion or all of the lead anchor 60. The recesses enable the distal portion 50 to maintain a lower profile on the lead anchor 60 as well as providing for a more secure mounting.

The distal portion 50 also includes one or more electrodes 56. The electrodes 56 can have any configuration as is known in the art. Exemplary electrode configurations can be found in the commonly assigned and co-pending application entitled "ELECTRODE CONFIGURATIONS FOR TRANSVASCULAR NERVE STIMULATION," assigned Ser. No. 11/668,957, which is herein incorporated by reference. In various exemplary embodiments of the present invention, the electrodes 56 can be ring or partial ring electrodes and can include a drug-eluting collar 58 adjacent the electrode 56. At least one electrode 56 is adapted to deliver an electrical pulse transvascularly to the nerve or muscle to be stimulated. According to one embodiment of the present invention, the distal portion 50 includes multiple electrodes 56 spaced an equal distance from one another along the distal portion 50. The electrodes 56 can have the same or differing polarities. Additionally, the electrodes 56 can be connected to multiple individual conductors through the lead body 42 allowing for them to be individually addressable. Individually addressable electrodes 56 allow for flexibility in electrode selection providing for greater control over the current field and the direction of stimulation as well as allowing for multiple options for stimulation and sensing.

According to one exemplary embodiment of the present invention, the lead anchor 60 is made from a superelastic material. Exemplary superelastic materials includes Nitinol, MP35N, and other materials well-known in the art. According to one embodiment of the present invention, the lead anchor 60 is formed from a laser-cut Nitinol tube using techniques generally known in the art. The Nitinol tube is cut with a laser to remove material leaving behind at least one collar having a diameter equal to that of the original tube diameter and one or more integrally formed, expandable struts. The struts can be connected forming one or more cells. Additionally, the struts can have a braided or non-braided configuration. According to an alternate embodiment of the present invention, the lead anchor 60 can be formed from one or more superelastic wires. Like the integrally formed struts, the wires can be connected to form one or more cells. As the number of cells increase, the anchor can take on a cage or basket like appearance. Additionally, the wires can have a braided or non-braided configuration. Finally, the wires can be spiraled, canted or arced and can have various configurations adapted to minimize the amount of strain on the wires.

According to one embodiment of the present invention, the lead anchor 60 includes at least one collar 76 secured to an end of the distal portion of the lead 6. As shown in FIGS. 3A-3D, the lead anchor 60 includes a proximal collar 76 secured to the first end 68 of the distal portion 50 of the lead 6 and a distal collar 80 secured to the second end 72. At least one expandable strut 84 extends from the proximal collar 76 to the distal collar 80. The expandable strut 84 is formed such that it is adapted to bias the distal portion 50 including the electrodes against a vessel wall of a vessel in which the distal portion 50 is deployed. According to another embodiment of the present invention, the lead anchor 60 includes a plurality of expandable struts 84 extending from the proximal collar 76 to the distal collar 80. According to a further embodiment of the present invention, as shown in FIGS. 3A-3D, the expandable struts 84 forming the lead anchor 60 include a proximal tapered region 88 connected to the proximal collar 76 and a distal tapered region 92 connected to the distal collar 80. The tapered regions 88 and 92 aid in delivery and retraction of the distal portion 50 of the lead 6.

Figure 4A:
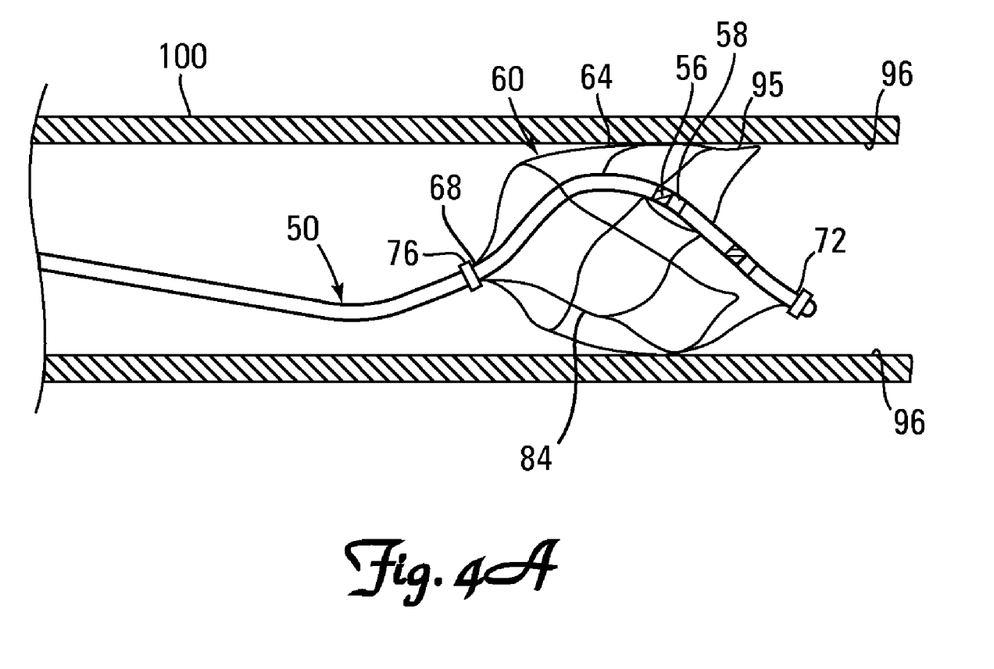
FIGS. 4A-4C are schematic views of a distal portion of a lead including a lead anchor having a single tapered end deployed within a vessel according to various embodiments of the present invention.
Figure 4B:
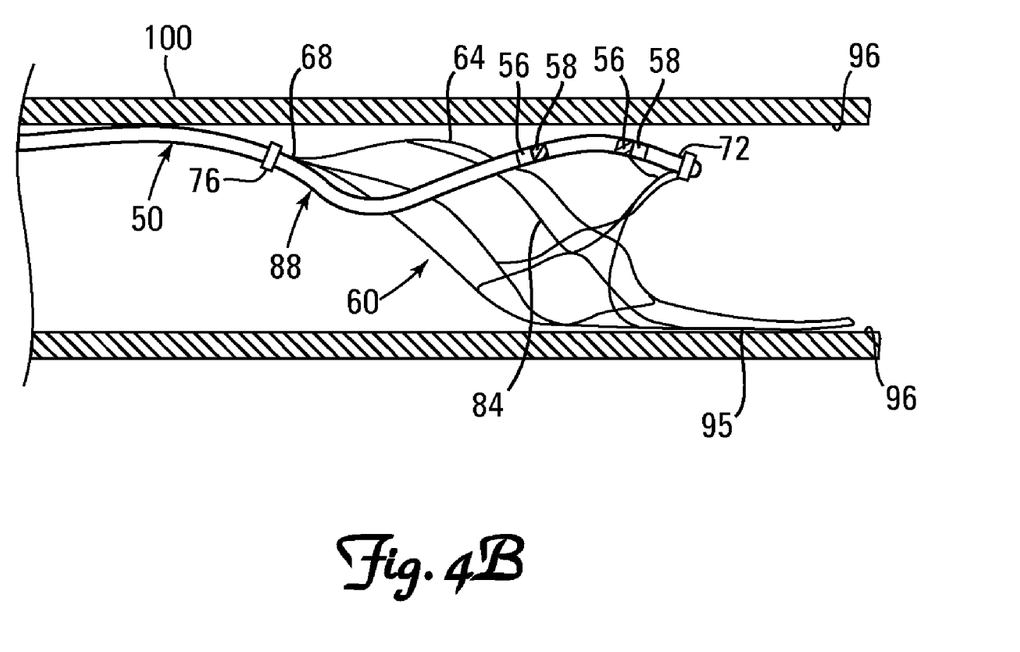
Figure 4C:
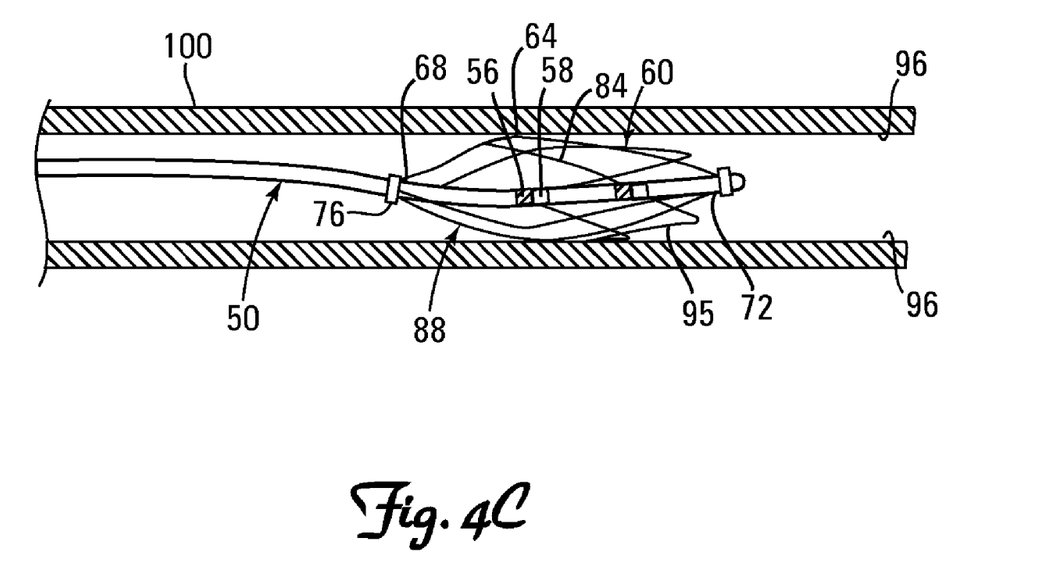

According to alternative embodiments of the present invention, as shown in FIGS. 4A-4C, the lead anchor 60 includes a single proximal collar 76 attached to the first end 68 of the distal portion 50. As shown in FIGS. 4A-4C, the lead anchor 60 includes a plurality of expandable struts 84 extending from the proximal collar 76 towards a distal end 72 of the distal portion 50. The expandable struts 84 include a tapered proximal region 88 connected at one end to the collar 76. The distal end 95 of the lead anchor 60 does not include a collar and thus the anchor 60 remains open-ended at its distal end 95.

According to a further embodiment of the present invention, the lead anchor 60 includes a biocompatible coating. According to various embodiments, the coating includes polyurethane, silicone, EFTE, PTFE, or another biocompatible material as is known in the art. According to another embodiment of the invention, the struts 84 can be individually coated with a biocompatible coating. According to yet a further embodiment of the present invention, a polymer sleeve covering the stent-like anchor 60 also can be utilized.

According to a further embodiment of the present invention, as shown in FIGS. 3A-4C, the lead anchor 60 is adapted to expand from a collapsed configuration to an expanded configuration. In the expanded configuration, the lead anchor 60 presses the distal portion 50 of the lead 6 and its electrodes 56 up against a vessel wall 96 of a vessel 100 in which the distal portion 50 of the lead 6 is deployed. The lead anchor 60 expands with sufficient radial force as to effectively minimize rotation and migration of the distal portion 50 including its electrodes 56 away from the target stimulation site, thus securing and stabilizing the distal portion 50 of the lead 6 within the vessel 100. Force is distributed along the expanded length of the anchor 60 providing for a more effective and stable anchoring mechanism. According to an embodiment of the present invention, the lead anchor 60 places enough radial expansion force on the vessel walls such that the distal portion 50 migrates outside of the original boundaries of the vessel walls 96 and towards the nerve 34 to be stimulated without damaging the vessel walls 96. As a result, any electrodes 56 located on the distal portion 50 are placed in closer proximity to the nerve 34. According to one exemplary embodiment of the present invention, the distance between the electrodes 56 and the nerve 34 to be stimulated is about less than 2 mm.

The migration of the distal portion 50 outside of the original boundaries of the vessel walls 96 causes no damage to the vessel walls 96 nor does the spiral erode through the vessel walls 96. A sheath of tissue forms over the distal portion 50 over an extended period of time such that it becomes encapsulated within the vessel walls 96. The outer geometry of the vessel 100 is altered such that the outline of the distal portion 50 of the lead 6 located within the vessel 100 is visible.

When expanded, a length of the lead anchor 60 ranges from about 6 to about 120 mm. Additionally, according to one embodiment of the present invention, an effective outer diameter of the expanded lead anchor 60 ranges from about 3 to about 40 mm. According to another embodiment of the present invention, the expanded lead anchor 60 has an effective outer diameter ranging from about 10 to about 25 mm. The size of the lead anchor 60 is selected such that, when in the expanded configuration, the lead anchor 60 has an outer diameter slightly larger than the inner diameter of the vessel 100 in which it is to be deployed. According to one exemplary embodiment, the outer diameter of the lead anchor 60 ranges from about 5 percent to 40 percent greater than the inner diameter of the vessel 100 in which the distal portion 50 is deployed. According to a further embodiment, the lead anchor 60 can be sized such that it can be used in conjunction with a lead adapted to be delivered to the left side of the heart as well as other locations within a patient's vasculature system.

Figure 5A:
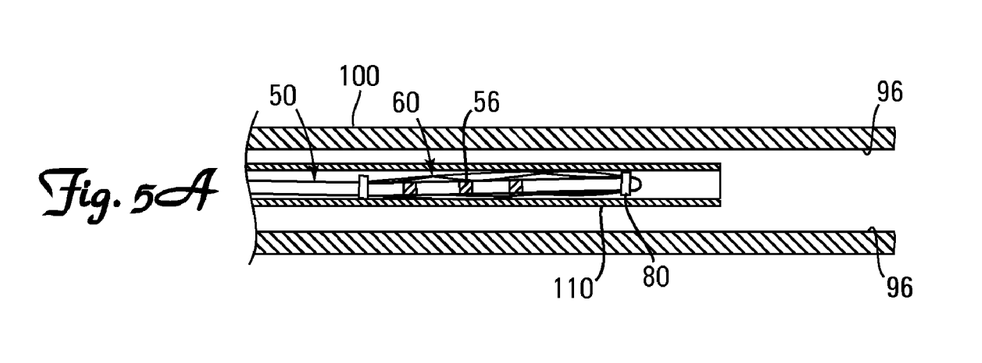
FIGS. 5A-5C are partial cross-sectional views of a lead including a lead anchor during delivery and deployment within a vessel according to an embodiment of the present invention.
Figure 5B:
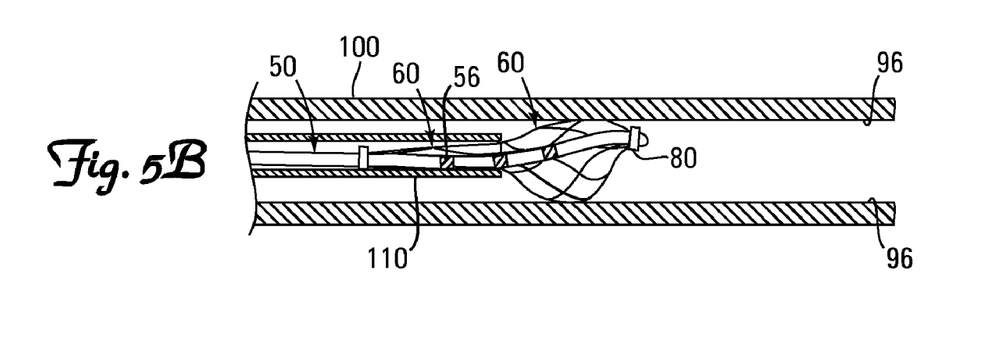
Figure 5C:
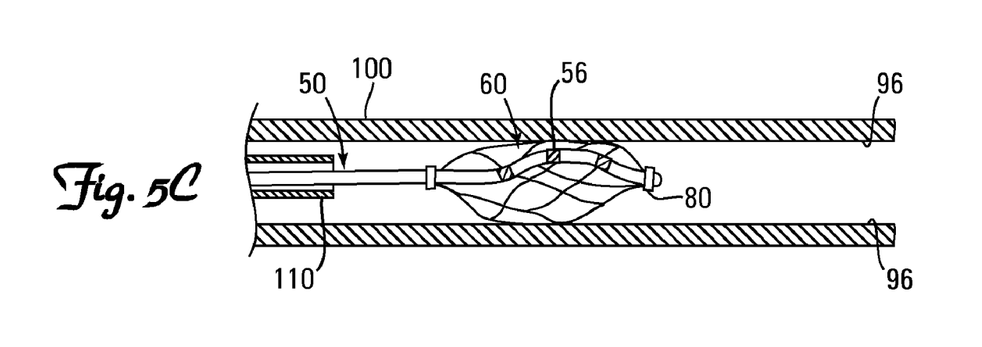

FIGS. 5A-5C show a distal portion 50 of the lead 6 during delivery and deployment within a vessel 100. In the collapsed configuration, as shown in FIG. 5A, the effective length of the distal portion 50 is substantially equal to the effective length of the lead anchor 60. According to one embodiment of the present invention, the collapsed lead anchor 60 including the distal portion 50 mounted thereto has an outer diameter ranging from about 1 to about 4 mm. According to one exemplary embodiment of the present invention, the collapsed lead anchor 60 has an overall length ranging from about 6 to about 200 mm. According to another embodiment of the present invention, the collapsed lead anchor has an overall length ranging from about 10 to about 80 mm.

According to one exemplary embodiment of the present invention, as shown in FIGS. 5A-5C, the lead anchor 60 is adapted to be retained within a guide catheter 110 or other suitable member capable of retaining the lead anchor 60 in its collapsed configuration for insertion and delivery within a patient's vasculature system, including any suitable vessel that is adjacent a nerve to be stimulated. According to another embodiment of the present invention, the lead body 42 can include a lumen adapted to receive a guiding element such as a stylet or a guide wire adapted to assist in delivery of the distal portion 50 including the lead anchor 60 to a stimulation site within a vessel. According to these embodiments, a stylet, guide wire, or guide catheter 110, either alone or in combination with one another, is used to collapse (either fully or partially) the distal portion 50 including the lead anchor 60 from an expanded configuration to a collapsed configuration (full or partial) and also to guide the distal portion 50 of the lead 6 through the patient's vasculature system to a stimulation site located within a vessel 100. In the collapsed configuration, as shown in FIG. 5A, the lead anchor 60 including the distal portion 50 mounted thereto can be inserted into a patient's vasculature system and guided to a stimulation site within a vessel 100.

According to a further embodiment of the present invention, as shown in FIGS. 5A-5C, a guide catheter 110 is used to deliver the lead anchor 60 including the distal portion 50 mounted thereto to the stimulation site within a vessel. Once inside the targeted vessel, as shown in FIG. 5B, the lead anchor 60 including the distal portion 50 can be partially deployed from the guide catheter 110 and rotated or otherwise manipulated. The electrodes 56 located on the distal portion 50 can be used to acutely stimulate and, thus, test potential stimulation sites. Once a stimulation site has been selected using the information gained through acute stimulation, the guide catheter 110 can be retracted and the lead anchor 60 fully deployed, as shown in FIG. 5C, so as to secure and stabilize the distal portion 50 of the lead 6 at a stimulation site within the vessel 100 such that transvascular stimulation of the adjacent nerve or muscle can occur.

According to yet another embodiment of the present invention, the lead anchor 60 is variably expandable. That is, the lead anchor 60 is adapted to expand with and adapt to the natural changes in the size and diameter of the vessel 100 while at the same time engaging and maintaining a frictional force on the vessel walls 96. For example, when in the internal jugular vein 18, 22, the internal geometry (diameter and inner shape) of the internal jugular vein 18, 22 may change with blood flow and blood pressure. Similarly, when a patient is in an upright position, the diameter of the vessel 100 may be smaller than when the patient is lying down or is in a prone position. The lead anchor 60 accounts for the difference in vessel diameter by expanding so as to maintain a frictional force on the vessel walls 96 securing and stabilizing the distal portion 50 in the vessel.

The distal portion 50 of the lead 6, according to various embodiments of the present invention, can be delivered to a stimulation site within a vessel adjacent a nerve, muscle, or tissue to be stimulated using standard techniques. According to one embodiment of the present invention, the lead 6 can be inserted in a patient's vasculature system via a percutaneous stick directly into a patient's internal jugular vein to deliver therapy to the vagus nerve. According to another embodiment of the present invention, the lead anchor 60, to which the distal portion 50 is mounted, is transitioned to a collapsed configuration and advanced through a patient's vasculature system and delivered to a stimulation site using a guiding element such as a guide catheter. Once the site has been reached and the guide catheter is retracted, the lead anchor 60 is allowed to transition from its collapsed configuration to its expanded configuration contacting and frictionally engaging the vessel walls of the vessel in which it is deployed. Likewise, a stylet or one or more guide wires may be inserted into a lumen located within the lead body 42 to transition the lead anchor 60 to transition from its predetermine expanded shape to a collapsed configuration. The distal portion 50 is then guided through the vasculature to a stimulation site located within a vessel. Once a stimulation site has been reached, the guide wire or stylet is removed allowing the lead anchor 60 to return to its predetermined shape. Pull wires can also be used to further expand the lead anchor 60 within a vessel such that the expandable struts 84 forming the anchor 60 place an additional radial force on the wall further securing and stabilizing the lead 6 within the vessel.

Whatever the delivery method, once the lead anchor 60 including the distal portion 50 mounted thereto has reached a stimulation site within a vessel 100 adjacent a nerve 34 to be stimulated, the lead anchor 60 expands forcing the distal portion 50 mounted to an exterior of the lead anchor 60 to contact and frictionally engage the vessel walls 96 of the vessel 100 in which the distal portion 50 including the lead anchor 60 is deployed. The lead body 42 and, thus, the lead anchor 60 can be rotated within the vessel 100 to orient the electrodes 56 towards the stimulation target. Additionally, the lead body 42 can be further rotated or positioned until a maximum or optimum electrical stimulation threshold by the electrodes 56 has been achieved across the vessel wall 96 to the adjacent nerve 34 or muscle to be stimulated. The stimulating pulse delivered by the electrodes 56 can then be measured to determine if an optimal stimulation threshold has been reached.

The distal portion 50 can be repositioned within the vessel by either rotating the lead body 42 within the vessel or reintroducing the guiding member such as the guide catheter 110 or guide wire to collapse (partially or fully) the lead anchor 60. The distal portion 50 mounted to an exterior of the lead anchor 60 can then either be repositioned and/or removed from the vessel 100. According to a further embodiment of the present invention, the distal portion 50 can be partially deployed from a guide catheter 110 in order to acutely stimulate the nerve. Once a suitable stimulation site has been identified using acute stimulation, the guide catheter 110 can be retracted and the lead anchor 60 including the distal portion 50 mounted to its exterior can be fully deployed within the vessel 100 at the stimulation site.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A medical electrical lead for stimulating a nerve, wherein the lead is adapted to be delivered to a stimulation site within a vessel adjacent the nerve to be stimulated, the lead comprising:
    a lead body including a proximal end adapted to be connected to a pulse generator, and a distal portion including a distal end;
    a plurality of conductors extending within the lead body from the proximal end thereof toward the distal end thereof;
    a plurality of individual ring electrodes longitudinally spaced along a length of the distal portion of the lead body and each coupled to one of the plurality of conductors; and
    a lead anchor having a first end secured to the distal portion of the lead body at a first location and a second end secured to the distal portion of the lead body at a second location distal to the first location, the lead anchor adapted to expand from a radially collapsed configuration to a preformed, radially expanded configuration, wherein the lead anchor has a first length between the first and second ends when in the radially collapsed configuration and a second length between the first and second ends when in the radially expanded configuration, the first length being greater than the second length, and
    wherein the plurality of individual ring electrodes are located between the first and second locations, and wherein the length of the distal portion of the lead body including the plurality of individual ring electrodes extends along and contacts an exterior of the lead anchor from the first end to the second end thereof such that in the radially expanded configuration the lead anchor is adapted to urge the length of the distal portion of the lead body against at least one vessel wall of a vessel in which the lead is deployed so as to secure and stabilize the distal portion of the lead within the vessel.

2. The medical electrical lead according to claim 1, wherein the vessel is selected from the group consisting of an internal jugular vein, a superior vena cava, or a brachiocephalic vein, and wherein the nerve is the vagus nerve.

3. The medical electrical lead according to claim 1, wherein the lead anchor comprises a superelastic material.

4. The medical electrical lead according to claim 1, wherein the lead anchor comprises at least one collar secured to the distal portion of the lead.

5. The medical electrical lead according to claim 1, wherein the lead anchor is formed from a laser cut tube of a superelastic material and comprises at least a first end secured to the lead body and a plurality of integrally formed struts extending from the first end to a second end.

6. The medical electrical lead according to claim 5, wherein the struts include a first tapered region tapering down and connected to a first end of the anchor secured to the lead body and a second tapered region tapering down and connected to a second end of the anchor secured to the lead body.

7. The medical electrical lead according to claim 5, wherein the struts include at least one tapered region tapering down and connected to an end of the anchor secured to the lead body.

8. The medical electrical lead according to claim 1, wherein the lead anchor comprises a first end radially offset from a second end.

9. The medical electrical lead according to claim 1, wherein the lead anchor comprises a first end radially aligned with a second end.

10. The medical electrical lead according to claim 1, wherein the lead anchor comprises a biocompatible coating.

11. The medical electrical lead according to claim 1, wherein the lead anchor comprises a polymer sleeve.

12. The medical electrical lead according to claim 1, wherein in the expanded configuration the lead anchor has an effective outer diameter ranging from about 3 to about 40 mm.

13. The medical electrical lead according to claim 1, wherein the lead anchor is configured to have an effective outer diameter in the radially expanded configuration of from about 5 percent to about 40 percent greater than an inner diameter of the vessel in which the distal portion of the lead is to be deployed.

14. A medical electrical lead for stimulating a nerve from within an adjacent vessel, the lead comprising:
    a lead body having a proximal end adapted to be connected to a pulse generator, and a distal portion including a distal end;
    a plurality of conductors extending within the lead body;
    a plurality of individual ring electrodes longitudinally spaced along a length of the distal portion of the lead body and each coupled to one of the plurality of conductors; and
    a lead anchor adapted to radially expand from a collapsed configuration to a preformed, radially expanded configuration and comprising a plurality of interconnected struts, the lead anchor having a first end connected to the distal portion of the lead body at a first location and a second end secured to the lead body at a second location distal to the first location, wherein the length of the distal portion of the lead body including the plurality of individual ring electrodes extends along and contacts an exterior of one of the struts from the first end to the second end of the lead anchor, and wherein the lead anchor has a first length between the first and second ends when in the radially collapsed configuration and a second length between the first and second ends when in the radially expanded configuration, the first length being greater than the second length.

15. The medical electrical lead according to claim 14, wherein a first length of the distal portion coupled to the exterior of the lead anchor is substantially equal to a length of the lead anchor when the lead anchor is in the collapsed configuration.

16. The medical electrical lead according to claim 14, wherein the lead anchor comprises a superelastic material.

17. The medical electrical lead according to claim 14, wherein the struts include a first tapered region tapering down and connected to the first end of the anchor secured to the lead body at the first location and a second tapered region tapering down and connected to the second end of the anchor secured to the lead body at the second location.

18. The medical electrical lead according to claim 14, wherein the struts include a first tapered region tapering down and connected to the first end of the anchor secured to the lead body at the first location.

19. The medical electrical lead according to claim 14, wherein the first end is radially offset from the second end.

20. The medical electrical lead according to claim 14, wherein the first end is radially aligned with the second end.

21. The medical electrical lead according to claim 14, wherein the lead anchor comprises a biocompatible coating.

22. The medical electrical lead according to claim 14, wherein the lead anchor comprises a polymer sleeve.

23. The medical electrical lead according to claim 14, wherein in the expanded configuration the lead anchor has an effective outer diameter ranging from about 3 to about 40 mm.

24. The medical electrical lead according to claim 14, wherein the lead anchor is configured to have an effective outer diameter in the radially expanded configuration of from about 5 percent to about 40 percent greater than an inner diameter of the vessel in which the distal portion of the lead is to be deployed.

25. The medical electrical lead according to claim 14, wherein the vessel is selected from the group consisting of an internal jugular vein, a superior vena cava, and a brachiocephalic vein and wherein the nerve is the vagus nerve.

* * * * *